United States Patent [19]

Kaneyoshi

[11] Patent Number: 5,417,206

[45] Date of Patent: May 23, 1995

[54] BLOOD CONSTITUENT MEASURING APPARATUS

[75] Inventor: Akio Kaneyoshi, Tokyo, Japan

[73] Assignee: NEC Corporation, Tokyo, Japan

[21] Appl. No.: 139,015

[22] Filed: Oct. 21, 1993

[30] Foreign Application Priority Data

Oct. 26, 1992 [JP] Japan .................. 4-310872

[51] Int. Cl.⁶ .............................................. A61B 5/00
[52] U.S. Cl. ...................................... 128/632; 604/313
[58] Field of Search ............... 128/760, 771, 632, 637;
604/313

[56] References Cited

U.S. PATENT DOCUMENTS 4,151,832  5/1979  Hamer ................................. 604/313
5,291,887  3/1994  Stanley et al. ....................... 128/632

FOREIGN PATENT DOCUMENTS 2-31740   2/1990  Japan .
2-286132 11/1990  Japan .

OTHER PUBLICATIONS

Patent Abstracts of Japan, vol. 16, No. 411 (CO979) Aug. 31, 1992.
Patent Abstracts of Japan, vol. 16, No. 092 (P-1321) Mar. 6, 1992.

Primary Examiner—Max Hindenburg
Attorney, Agent, or Firm—Foley & Lardner

[57] ABSTRACT

A sampling cell (1) sucks body fluid, which is suction effusion fluid (SEF), into a passage by decompressive suction. At this time, the inside of the passage is under reduced pressure and accordingly the SEF contains a large amount of bubbles of oxygen and other gases. When, in this state, first opening/closing means (20, 21) provided in part of the passage are closed and third opening/closing means (25) is opened to bring the passage filled with the SEF into communication with the atmosphere, the gases contained in the SEF are discharged into the atmosphere. After that, the SEF in the passage, cleared of the gases, is supplied together with buffer solution to measuring means (7). Therefore, the SEF to be fed to the measuring means (7) can be supplied always in a fixed quantity.

5 Claims, 3 Drawing Sheets 5,417,206

BLOOD CONSTITUENT MEASURING APPARATUS

BACKGROUND OF THE INVENTION

1. Field of the Invention

The present invention relates to an apparatus for measuring blood constituents, and more particularly to an apparatus for measuring blood constituents by utilizing suction effusion fluid (SEF) obtained by sucking the surface of skin deprived of the keratinous layer.

2. Description of the Prior Art

According to the prior art, when a blood constituent, for instance blood-sugar, is to be measured, it can be done either with blood sampled from a blood vessel or by sampling body fluid containing the blood constituent from under the skin by decompressive suction and measuring the concentration of glucose contained in the SEF with a glucose sensor. Examples of apparatus for measuring blood constituents by utilizing SEF are disclosed in the Japanese Patent Disclosure Gazettes No. 2-31740 published on Feb. 1, 1990 and No. 2-286132 published on Nov. 26, 1990. These apparatuses have the advantage of making it possible to sample body fluid containing the desired blood constituent with no pain to the subject.

FIG. 4 shows a cross section of a blood constituent measuring apparatus embodying the common elements of the aforementioned two examples of the prior art. In the figure, the blood constituent measuring apparatus includes a sampling cell 51 and a measuring section 57 for measuring the concentration of glucose in SEF obtained by suction with the sampling cell 51. The sampling cell 51 consists of a head 52 which comes into contact with skin S, a box 53 solidly linked to the head 52, and a measuring member 54 installed to be rotatable via drive means (not shown) within the box 53. The cylindrical measuring member 54 is rotatable around its center axis (in a direction normal to the surface of the drawing).

Within the head 52 and the measuring member 54 are formed passages 52A and 54A for sucking SEF, which are so arranged as to extend on coaxial lines when decompressive suction is performed.

To the center of the upper face of the box 53 is connected a tube 55 linked to a pump for decompressive suction (not shown), and this tube 55 is so arranged as to be in communication with the passage 54A of the measuring member 54. To the left and right faces of the box 53 are respectively connected a buffer solution feed pipe 56 for supplying buffer solution and an SEF feed pipe 58 for supplying SEF together with the buffer solution to the measuring section 57. The buffer solution feed pipe 56 and the SEF feed pipe 58 are so arranged on the same axis as to permit communication between each other when the passage 54A has reached a substantially horizontal position as a result of the rotation of the measuring member 54 in direction C in the drawing. After the measurement is completed, the SEF is discharged through a pipe 60 together with the buffer solution.

In the above-described configuration, when body fluid containing the desired blood constituent is to be sucked from under the skin, the head 52 of the sampling cell 51 is brought into contact with the surface of skin S, and the passage 54A of the measuring member 54 is so set as to be on the same axis with the passage 52A of the head 52 and with the tube 55.

Then, as the pump for decompressive suction (not shown), connected to one end of the tube 55, is operated to reduce the pressure in the passages 52A and 54A and the tube 55, body fluid containing the desired blood constituent effuses from the surface of skin S into the passages 52A and 54A. When the SEF effusing in this manner has accumulated to a prescribed amount, the measuring member 54 is rotated in direction C to a substantially horizontal position. In this state, the passage 54A in the measuring member 54 is aligned on the same axis with the buffer solution feed pipe 56 and the SEF feed pipe 58; a prescribed amount of buffer solution is supplied to the passage 54A side from the buffer solution feed pipe 56 and, together with the SEF in the passage 54A, supplied to the measuring section 57 of the next stage via the SEF feed pipe 58. During this process, the inside of the measuring section 57 is maintained at normal pressure.

The SEF supplied to the measuring section 57 is subjected by a sensor 59 to prescribed measurement or analysis and, after its completion, discharged externally through the pipe 60 connected to the measuring section 57.

However, since this blood constituent measuring apparatus according to the prior art samples SEF by decompressive suction, the SEF is subject to the presence of bubbles resulting from cutaneous respiration or attributable to oxygen and other gases contained in the SEF itself, and the volume of the gaseous contents of the SEF becomes greater than under normal pressure.

Therefore, in the blood constituent measuring apparatus according to the prior art, which samples SEF under reduced pressure, the volume of bubbles in the passage 54A of the measuring member 54 becomes greater than the volume under normal pressure, however, the bubbles contract when the SEF is supplied to the measuring section 57 under normal pressure, and accordingly the total volume of the SEF obtained eventually becomes much smaller than what it was in the passage 54A of the measuring member 54 and the accuracy of measurement or analysis is thereby affected seriously.

SUMMARY OF THE INVENTION

The present invention has been undertaken in view of this disadvantage of the prior art, and its object is to provide a blood constituent measuring apparatus capable of liberating the gaseous contents of suction effusion fluid (SEF) into the atmosphere and obtaining a necessary and sufficient volume of SEF for measuring or analyzing the desired constituent of blood.

According to the invention, there is provided a blood constituent measuring apparatus comprising a sampling cell having a passage in which is accumulated SEF obtained by sucking skin under reduced pressure with the cell kept in close contact with the skin; first opening/closing means for forming a closed passage by closing both ends of the passage in a decompressed state in which the SEF has accumulated; second opening/closing means for releasing the decompressed state of the closed passage; discharging means for discharging, after the operation of the second opening/closing means, the SEF in the closed passage together with buffer solution; and measuring means for measuring a specific blood constituent in the SEF from its mixture with buffer solution discharged from the discharging means.

The sampling cell sucks body fluid, which is the SEF, by decompressive suction into its passage, when the inside of the passage is under reduced pressure and accordingly the SEF contains a large amount of bubbles of oxygen and other gases. When, in this state, the first opening/closing means provided in part of the passage is closed and second opening/closing means is opened to bring the passage filled with the SEF into communication with the atmosphere, the gases contained in the SEF are liberated into the atmosphere. After that, the SEF in the passage, cleared of the gases, is supplied together with the buffer solution to the measuring means. Therefore, the SEF to be fed to the measuring means can be supplied always in a fixed quantity.

BRIEF DESCRIPTION OF THE DRAWINGS

The above-mentioned and other objects, features and advantages of the present invention will become more apparent from the following detailed description when taken in conjunction with the accompanying drawings, wherein.

DETAILED DESCRIPTION OF THE PREFERRED EMBODIMENT

Figure 1:
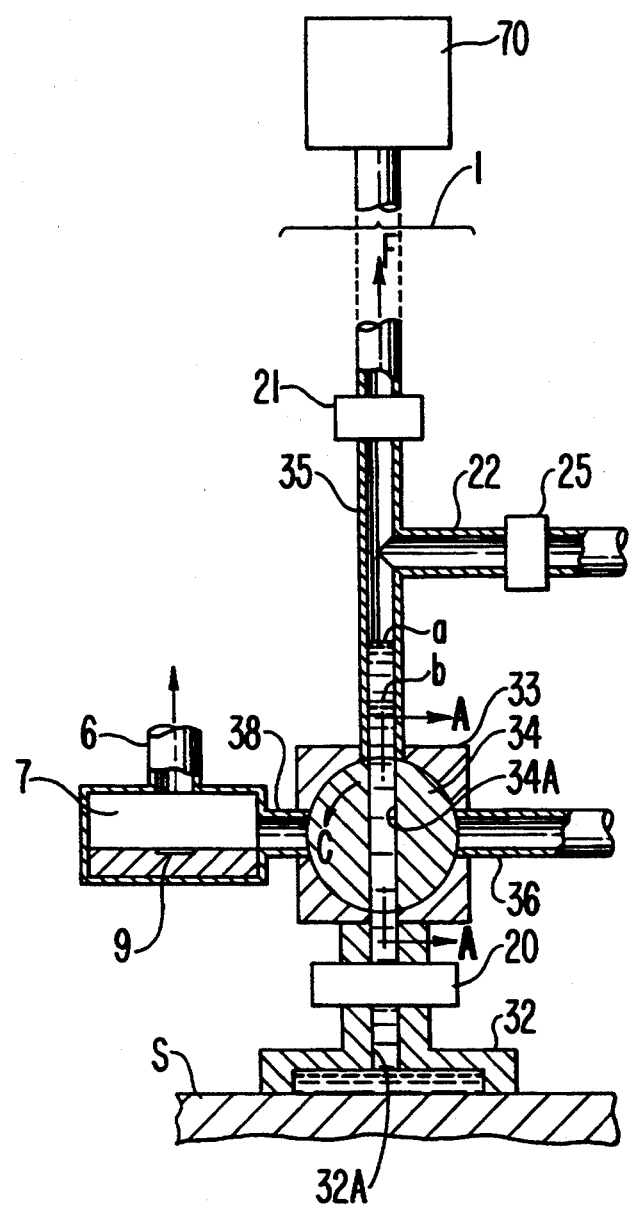
FIG. 1 is a cross sectional view of a blood constituent measuring apparatus according to a preferred embodiment of the invention.
Figure 2:
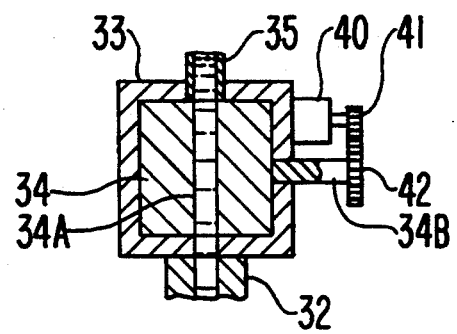
FIG. 2 is an A—A cross sectional view of FIG. 1.

FIG. 1 shows a cross section of a preferred embodiment of the present invention, and FIG. 2 shows the A—A cross section of FIG. 1.

Figure 4:
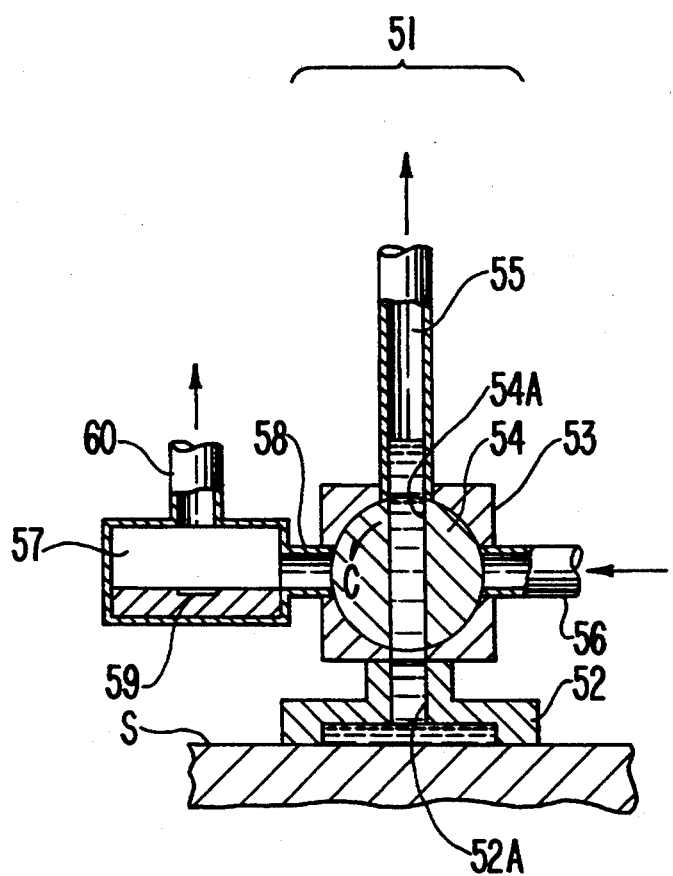
FIG. 4 is a cross sectional view of a blood constituent measuring apparatus according to the prior art.

In the figure, the blood constituent measuring apparatus includes a sampling cell 1 for sucking body fluid containing blood constituents under reduced pressure; a measuring section 7 for measuring a specific blood constituent in the SEF sampled by the sampling cell 1; first and second electromagnetic valves 20 and 21 as first opening/closing means for closing the passage in the sampling cell 1 with its decompressed state kept as it is; and a third electromagnetic valve 25 as second opening/closing means for bringing the pressure in the passage between the electromagnetic valves 20 and 21 to the atmospheric level. The sampling cell 1 has a head 32 which comes into contact with skin S, an accumulating member 34 which is a rotatable member, a box 33, and a tube 35, and these constituent elements are substantially the same as the corresponding items used in the sampling cell 51 of the blood constituent measuring apparatus according to the prior art, illustrated in FIG. 4. To one end of the tube 35 is connected a suction pump 70 for reducing the pressure in the passage within the sampling cell 1 to 400 mm Hg.

As illustrated in FIG. 2, the accumulating member 34 is a metallic cylinder housed in the box 33, and a member rotating shaft 34B is fixed on the center axis of the cylinder. A motive power from a motor 40, fixed to the box 33, is transmitted via gears 41 and 42 to the bulb rotating shaft 34B to turn the cylinder. A passage 34A having a diameter of no more than 1 mm, in which SEF is to be accumulated, is formed in a direction normal to the member rotating shaft 34B, and can hold 5 $\mu l$ of SEF. The head 32 and the tube 35 are connected on the same axis via the passage 34A as shown in FIG. 1. As the accumulating member 34 is rotated 90° in the direction of arrow C in FIG. 1 by the motor 40 and the passage 34A comes horizontal, passages 36 and 38 are connected to the passage 34A on the same axis to be linked to the measuring section 7. However, before the accumulating member 34 rotates in the direction of arrow C, the electromagnetic valves 20, 21 and 25 of the sampling cell 1 operate.

The first electromagnetic valve 20 is arranged midway of the passage 32A in the head 32, while the second electromagnetic valve 21 is arranged midway of the tube 35. Midway of the tube 35 and between the valve 21 and the box 33 is provided a branching tube 22, midway of which is arranged the third electromagnetic valve 25.

Figure 3:
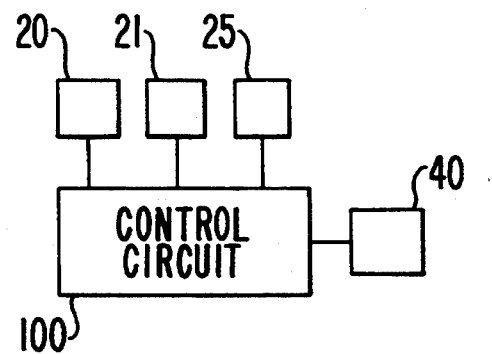
FIG. 3 is a block diagram of a drive control circuit for driving the blood constituent measuring apparatus of FIG. 1.

These electromagnetic valves 20, 21 and 25 are appropriately opened or closed by a control circuit 100 illustrated in FIG. 3. This control circuit 100 also controls the drive of the motor 40.

Next will be described the operation of this preferred embodiment of the present invention.

Initially, the measuring member 34 is so set that its passage 34A fall on the same axis of the passage 32A of the head 32. At the same time, the control circuit 100, while opening the first and second electromagnetic valves 20 and 21, closes the third electromagnetic valve 25. Hereupon, the pump 70 for decompressive suction is actuated to start suction in the direction of arrow F in FIG. 1.

In a prescribed period of time after the start of suction, in two minutes in this particular embodiment, SEF fills the passage 34A of the accumulating member 34, and its level reaches position a. In this state, however, the inside of the passages 32A and 34A and the tube 35 is under reduced pressure, and therefore the SEF contains many bubbles. Hereupon the control circuit 100 closes the first and second electromagnetic valves 20 and 21 and opens the third electromagnetic valve 25. The pressure in the passages 32A and 34A and the tube 35 between the first and second electromagnetic valves 20 and 21 is thereby brought to the atmospheric level. Thus, as the gas forming the bubbles in the SEF is discharged into the atmosphere, the SEF level in the passages 32A and 34A is brought down to position b. Since the first and second electromagnetic valves 20 and 21 are closed at this time, the surface of skin S under the head 32 remains under reduced pressure and the pressure on the decompressive suction pump 70 also is at the reduced level, and there scarcely is the need to perform suction again for SEF sampling.

Then, the control circuit 100 drives the motor 40 to rotate the measuring bulb 34 in the direction of arrow C until the passage 34A becomes substantially horizontal, and a fluid feed pump (not shown) supplies buffer solution via the buffer solution feed pipe 36 to the passage 54A side. At this time, fixed amounts of SEF and of buffer solution, containing virtually no bubbles, are mixed in a fixed ratio, and the mixture is fed to the measuring section 7 via the SEF feed pipe 38. Then it is made possible for a sensor 9 in the measuring section 7 to measure or analyze glucose contained in the SEF. For the sensor 9, an ion-sensitive field effect transistor glucose is the most suitable.

Here, although the SEF before the mixing of the buffer solution is in a very small amount, only 5 $\mu l$, its oxygen concentration is low and its pH level and pH buffer capacity are variable, the mixing of the buffer solution of which the oxygen concentration is high and the pH level and pH buffer capacity are constant makes it possible to accurately measure the glucose concentration. As buffer solution, 20 mM HEPES (N-2-hydroxyethylpiperazin-N'-2-ethane sulphonic acid, pH 7.5, 0.15 in ion intensity) is used, for example. Into the measuring section 7 enter the buffer solution and the SEF of 40 μl in combined quantity to be measured by the sensor 9.

After the completion of measurement, buffer solution is supplied again to discharge through a pipe 6 the fluid having accumulated in the measuring section 7 and to wash the sensor 9 at the same time.

If SEF is to be sampled again, the control circuit 100 turns the motor 40 in the reverse direction to return the accumulating member 34 to its initial state, closes the third electromagnetic valve 25, and opens the first and second electromagnetic valves 20 and 21. The pressure in the passage 34A of the accumulating member 34 and the tube 35 is thereby returned to the reduced level, making it possible to sample SEF again.

Thus, in the above-described preferred embodiment, as the first and second electromagnetic valves 20 and 21 are provided midway of the passage 32A of the head 32 and the tube 35, respectively, and the branching tube 22 is separately arranged and provided with the third electromagnetic valve 25 as its opening means, gas contained in the SEF having effused into the passage 34A of the accumulating bulb 34 is discharged into the atmosphere. Therefore, as long as SEF is sampled in a quantity in excess of the equivalent of the fluid level drop resulting from the gas discharge, the total quantity of SEF supplied to the measuring section 7 can be kept constant all the time, and accordingly sufficient sampling for the prescribed measurement or analysis in the measuring section 7 is made possible.

Moreover, the arrangement of the first and second electromagnetic valves 20 and 21 makes the configuration capable of opening a limited area to the atmosphere without returning the pressure on the skin S surface side and the decompressive suction pump side to the normal level, resulting in an effect to prevent otherwise unnecessary repeating of suction. Furthermore, as the overall configuration can be realized without modifying the design of the conventional structure to a substantial extent, the addition to the manufacturing cost of any prior art apparatus can be minimized.

Incidentally, the electromagnetic valve 25 as second opening/closing means is not limited to this example, but a valve of various other structures can be used as long as it can open the pressure in the passage 34A and the tube 35 to the atmosphere. Although the accumulating member 34 in this embodiment is a metallic cylinder, its shape is not restricted to this example, but may be bulbous.

Since the present invention provides for the above-described configuration and operation, it can provide an SEF sampling apparatus having the unprecedented effect of enabling bubbles contained in sampled SEF to be liberated into the atmosphere and securing a necessary and sufficient quantity of SEF for measuring or analyzing the desired blood constituent.

Furthermore, although the invention has been fully described by way of a specific embodiment thereof with reference to the accompanying drawings, various changes and modifications will be apparent to persons skilled in the art. Therefore unless these changes and modifications otherwise depart from the scope of the present invention, they should be construed as included therein.

What is claimed is:

1. A blood constituent measuring apparatus for measuring blood constituents in suction effusion fluid (SEF) obtained from the surface of skin deprived of the Keratinous layer, comprising:
   a sampling cell having a head which is brought in close contact with the skin during operation of said blood constituent measuring apparatus, an accumulating member which has a passage connected to said head to accumulate the SEF obtained by sucking the surface of the skin in a decompressed state via said head, and a tube which is connected to said passage and is used to generate said decompressed state;
   a first valve which is deposed between said head and said accumulating member;
   a second valve which is connected along said tube;
   a third valve which is connected to said tube between said accumulating member and said second valve for discharging gas contained in the SEF accumulated in said passage through said third valve into a decompressed atmosphere; and
   measuring means for measuring a blood constituent in the SEF accumulated in said passage by combining the SEF with a buffer solution;
   wherein said first and second valves open and said third valve closes while the SEF is sucked from the skin in said decompressed state, and said first and second valves close and said third valve opens to decompress said passage to discharge the gas contained in the SEF into the decompressed atmosphere.

2. The blood constituent measuring apparatus, as claimed in claim 1, wherein said accumulating member rotates in said sampling cell to connect said passage to said measuring means.

3. The blood constituent measuring apparatus, as claimed in claim 1, wherein said first, second and third valves consist of electromagnetic valves, and wherein said apparatus further comprises control means for controlling said electromagnetic valves.

4. The blood constituent measuring apparatus, as claimed in claim 1, wherein said measuring means includes a sensor for detecting a concentration of glucose in said SEF.

5. The blood constituent measuring apparatus, as claimed in claim 4, wherein said buffer solution contains a constituent for assisting said sensor in detecting the glucose.

* * * * *